(12) United States Patent
Rosenblatt

(10) Patent No.: US 8,109,867 B2
(45) Date of Patent: Feb. 7, 2012

(54) TUBULAR MESH FOR SACROCOLPOPEXY AND RELATED PROCEDURES

(75) Inventor: Peter L. Rosenblatt, Newton, MA (US)

(73) Assignee: Rosenblatt Associates, LLC, Newton, MA (US)

( * ) Notice: Subject to any disclaimer, the term of this patent is extended or adjusted under 35 U.S.C. 154(b) by 0 days.

(21) Appl. No.: 12/790,453

(22) Filed: May 28, 2010

(65) Prior Publication Data

US 2010/0305394 A1    Dec. 2, 2010

Related U.S. Application Data

(60) Provisional application No. 61/217,161, filed on May 28, 2009.

(51) Int. Cl.
*A61F 2/00*    (2006.01)
(52) U.S. Cl. .................................... 600/37; 600/30
(58) Field of Classification Search ............. 600/29–32, 600/37; 606/151, 152–155; 623/23.64–23.76; 128/897–898
See application file for complete search history.

(56) References Cited

U.S. PATENT DOCUMENTS

| | | | |
|---|---|---|---|
| 6,575,897 B1 | 6/2003 | Ory et al. | |
| 6,592,515 B2 | 7/2003 | Thierfelder et al. | |
| 6,695,855 B1 | 2/2004 | Gaston | |
| 2002/0028980 A1 | 3/2002 | Thierfelder et al. | |
| 2002/0147382 A1* | 10/2002 | Neisz et al. | 600/29 |
| 2003/0023137 A1* | 1/2003 | Gellman | 600/30 |
| 2004/0138747 A1 | 7/2004 | Kaladelfos | |
| 2006/0122457 A1* | 6/2006 | Kovac et al. | 600/37 |
| 2007/0156175 A1* | 7/2007 | Weadock et al. | 606/216 |
| 2008/0021265 A1 | 1/2008 | Garbin et al. | |

FOREIGN PATENT DOCUMENTS

WO    03073960 A1    9/2003

* cited by examiner

*Primary Examiner* — Charles A Marmor, II
*Assistant Examiner* — Carrie R Dorna
(74) *Attorney, Agent, or Firm* — Scott E. Kamholz; Foley Hoag LLP

(57) ABSTRACT

A sacrocolpopexy mesh that includes lateral support to improve vaginal contact during colpopexy and to prevent slipping.

13 Claims, 6 Drawing Sheets

TUBULAR MESH FOR SACROCOLPOPEXY AND RELATED PROCEDURES

CROSS-REFERENCE TO RELATED APPLICATION

This application claims the benefit of U.S. provisional application Ser. No. 61/217,161, filed May 28, 2009, which is hereby incorporated herein by reference.

BACKGROUND

Sacrocolpopexy remains the gold standard treatment of post-hysterectomy vaginal vault prolapse. Sacrocolpopexy is usually performed through an abdominal incision, although more recently, laparoscopic and robotic sacrocolpopexy has been utilized by pelvic reconstructive surgeons to reduce the morbidity associated with laparotomy. Sacrocolpopexy involves suspension of the vagina to the sacrum using an intervening graft material. Various materials have been used in this procedure, including both natural and synthetic materials, although permanent synthetic mesh is most often described, due to excellent long-term results described in the literature. Of the synthetic materials in use today, the most commonly used is type I, macroporous, monofilament, lightweight polypropylene. This material is well tolerated, easy to handle, and resistant to infection and erosion through tissues in the pelvis, especially the vagina. Most surgeons who perform sacrocolpopexy employ a "Y-shaped" configuration of the mesh. This configuration includes two extensions of the mesh that provide coverage to the posterior and anterior vaginal walls. During the surgery, the bladder is advanced off the anterior vagina and the rectum is dissected free of the posterior vagina by entrance into the rectovaginal septum. The mesh arms and then placed over the anterior and posterior vagina and sutured in place with multiple interrupted sutures. Once the vaginal sutures have been placed, the surgeon attaches the mesh to the anterior longitudinal ligament of the sacrum, either at the promontory or lower, in the hollow of the sacrum. Finally, some surgeons choose to bury the mesh under the peritoneum, to prevent the potential development of internal intestinal hernia and subsequent obstruction.

Management of the mesh arms can be somewhat challenging during surgery, especially during laparoscopic or robotic sacrocolpopexy. It is important to allow the mesh to lie down flat against the endopelvic vaginal fascia, so that it does not bunch up, which is felt to be a risk factor for dyspareunia, infection, mesh exposure, erosion and pain. There is a need for a mesh configuration that will assist surgeons in the performance of sacrocolpopexy.

A similar procedure can be performed with the uterus in place (sacrohysteropexy) or with the cervix in place after supracervical hysterectomy (sacrocervicopexy). With the latter procedure, access to the peritoneal cavity can be accomplished through the vagina and cervix, through a cannula placed transvaginally. Using that method, the mesh can be introduced through the cervical trocar and needles with suture can also be introduced and removed in this manner. There is also a need to develop a mesh configuration that can be used with sacrocervicopexy that can accommodate a transcervical access port.

SUMMARY

The present disclosure describes a novel mesh design that solves the problems identified above. The extension from the vagina to the sacrum remains 2-dimensional, but the part of the mesh that attaches to the vagina has a tubular or conical shape. By creating a conical-shaped mesh that may surround the vaginal canal, the mesh will be easier to place and suture against and less likely to bunch up in particular areas. One feature of the conical mesh is that it can be customized to fit the individual patient's anatomy. For instance, if the anterior segment of the endopelvic fascia is shorter than the posterior segment (as is often the case), the anterior portion can be trimmed, either before or after insertion into the abdomen. In some women, an area for suturing the mesh can be created anteriorly and posteriorly, but not as much laterally, where bladder pillars and/or remnants of the cardinal and uterosacral ligaments may be located and prevent suturing. In this case, the lateral portions of the tubular mesh can be trimmed. As long as some aspect of lateral tubular mesh remains, the mesh will tend to conform to the proper shape and will expedite suture placement and prevent rolling and bunching of the mesh. Following placement of one or more fixation sutures, this lateral mesh may be left in place, may be incised, or may be excised with laparoscopic scissors.

The configuration of the mesh may be more of a traditional "Y-shaped" form, but may have added lateral elements that create a tubular configuration, that help keep the mesh in place during suturing, and may be removed, if desired, at the completion of the procedure.

The tubular mesh may also be used for sacrocervicopexy, where the cervix is used as an access site for insertion and removal of surgical devices, such as mesh, sutures, and needles, in order to avoid the use of larger abdominal access ports, which is associated with greater post-operative discomfort and greater potential for hernia complications. In order to use the tubular mesh design for this purpose, an open access area is required at the apex of the vaginal mesh portion.

The present mesh configuration may also have the ability to self-attach to the vaginal wall with the use of one or more elements on the inner lining of the tubular mesh configuration, including suture barbs, absorbable or non-absorbable projections or adhesives.

The present mesh configuration may be used with one or more vaginal probes that correspond in shape with one or more sizes of tubular mesh. The probes assist with delineating the vagina, and assist with suturing the mesh to the vaginal wall. A probe designed with a central access port may also be used for laparoscopic or robotic sacrocervicopexy (after supracervical hysterectomy), for insertion and removal of surgical devices, such as mesh, sutures and needles into and out from the abdominal/pelvic cavity.

DETAILED DESCRIPTION

Figure 1:
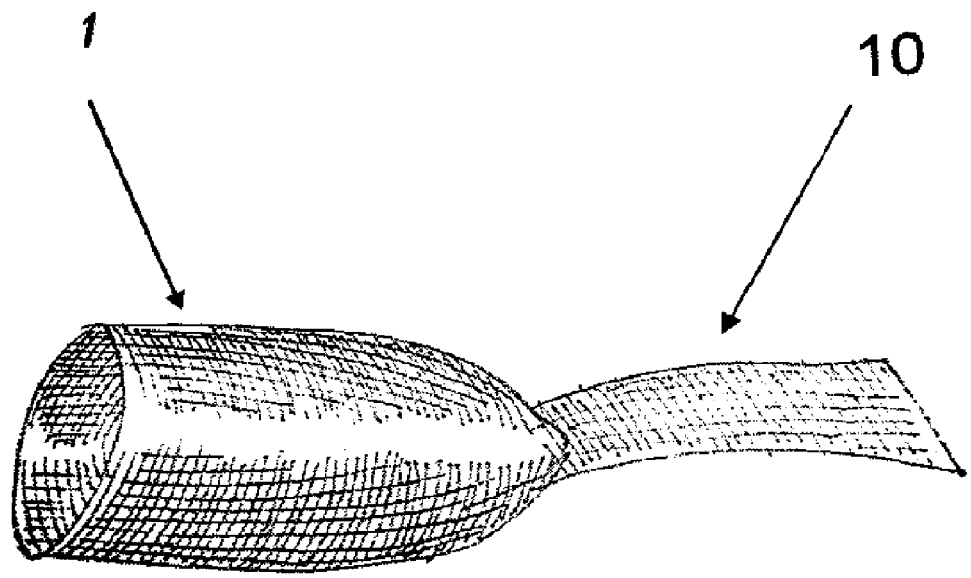
FIG. 1 demonstrates the basic configuration of the tubular mesh for sacrocolpopexy.

The present disclosure provides a system for performing sacrocolpopexy, whether it is performed open, laparoscopically or robotically. The system has two components: 1. a tubular or conical mesh configuration for covering the vagina, to facilitate suturing the mesh to the vagina, and an extension to the sacrum, to provide apical support, and 2. one or more vaginal probes to delineate the vagina when viewed internally.

The sacrocolpopexy mesh may be in a tubular or conical configuration, so that it encircles the vaginal tube, allowing it to lay flat against the vaginal canal, which would facilitate suturing. Alternatively, the mesh may have an anterior and posterior extension, and may have rounded distal edges. The mesh may have some continuation laterally, at least proximally along the vaginal wall, so that the mesh maintains contact with the vaginal tube, in a manner similar to fitting a sock on a foot or a glove on a hand.

An alternative configuration of the mesh could be a more traditional "Y-shaped" form, but with some material providing some lateral attachment between the anterior and posterior mesh extensions. In one embodiment, the lateral material may be made of the same mesh material as the Y-shaped mesh, or may be a material with greater elasticity, so that it conforms better to the shape of the vagina. This lateral material (on one or both sides) could either be left in place, or could be removed after placement of the fixation sutures. The lateral attachments may be attached to the body of the mesh in such a way so that they can be removed simply, such as by cutting a single suture that is woven into the mesh that would release the lateral attachment from the Y-shaped mesh body.

Alternatively, a single or series of elastic or non-elastic sutures that attach the anterior and posterior mesh extensions could be removed after placement of the fixation sutures anteriorly and posteriorly. For example, a "zig-zag" pattern of suture could be used to attach the anterior and posterior mesh extensions, and this suture could be removed by cutting the suture, which would unravel the lateral attachment. This would then be accomplished on the contralateral side. In another embodiment, a single or series of elastic sutures or bands can be attached to or near the distal edges of the tubular mesh, and this would facilitate placement of the mesh over the circumference of the vagina. This technique could also be used with a more traditional Y-shaped mesh, and this suture or elastic band could be removed after one or more fixation sutures have been placed.

For cases of sacrocervicopexy, one of two possible configurations of mesh are contemplated. In one embodiment, the same configuration described may be used, and the mesh and needles are introduced through either an abdominal incision (abdominal sacrocervicopexy) or a laparoscopic port site. Alternatively, the tubular mesh configuration could have an access area for introduction of mesh and other materials in and out of the pelvic cavity. This access area may be a hole in the mesh, and may be reinforced to prevent tearing of the mesh. The access area may also be a flap of mesh that can be sutured or otherwise repaired following completion of the procedure. The access area may also be a slit (which may also be reinforced) in the proximal portion of the vaginal mesh. This configuration of mesh, with a fenestration at the apical portion of the vaginal aspect of the mesh, can also be used for sacrocolpopexy, should the surgeon wish to make a small incision at the apex of the vagina for the introduction of surgical devices, such as mesh, sutures, or needles into the abdominal/pelvic cavity, during laparoscopic or robotic surgery.

The material used for the mesh may be a synthetic material with some degree of elasticity to conform to the shape of the vagina. Monofilament macroporous polypropylene is the preferred material but other synthetic non-absorbable and absorbable materials, such as polyester, silk, polydioxinone and polygylcolic acid are alternative options, as well as natural grafts, such as porcine dermis and small intestinal submucosa.

The synthetic mesh itself may be made of one of several materials, though the preferred material is Type I, macroporous, monofilament polypropylene, and would have such a configuration as to allow some elasticity so that it could conform to the outer topography of the patient's vaginal vault. Even if the surgeon decided to trim a good portion of the lateral mesh, the remainder of the mesh would maintain its tubular shape so that it conforms to the shape of the vagina. The extension of mesh that is used to suture the mesh to the sacrum may narrow after the take-off from the apex, to facilitate burying the mesh under the peritoneum at the end of the sacrocolpopexy. The extension may also have colored markings to be used by the surgeon as a "measuring tape" that may assist with determining the tension on the mesh.

Another embodiment of this mesh configuration is one that has suture barbs that are unidirectional on the inner portion of the tubular mesh. Such barbs have been used successfully for monofilament suture (Quill™ SRS, Angiotech Pharmaceuticals, Inc., Vancouver, BC, Canada), which allows placement without knot tying. This would allow the tubular mesh to be placed on to the vaginal wall (after dissecting the bladder and rectum free of the vagina) without friction, but once in place, the barbs (which may be located on the most distal edges of the mesh or placed throughout the inner surface area of the tubular mesh) would grab onto the vaginal wall. Tension in the mesh from sacral attachment would help maintain the grip. This may obviate the need to use any fixation sutures to attach the mesh to the vagina, or may reduce the number of fixation sutures needed to hold the mesh in place. The barbs may be microscopic slits in the monofilament strands of the mesh; alternatively, they may be molded projections that extend for a short distance from the mesh and latch on to the vaginal wall. The attachment of the barbs (and therefore the mesh) to the vagina may be facilitated by a solid vaginal probe placed in the vagina during, and potentially after, surgery. Other surfaces with increased grip may be employed, such as textured surfaces, roughened surfaces, laser-etched surface, or other treatments to increase friction.

During sacrocolpopexy surgery, a solid probe may be placed in the vagina to delineate the vaginal walls. This probe may be oblong, having a flatter anterior and posterior surface (i.e. wider) and narrower between the anterior and posterior surfaces. There may be several sizes of probes available to fit the individual patient. It may be desirable to have various sizes of tubular mesh configurations, so that the mesh can conform to one of the probes placed vaginally. Alternatively, the elasticity of the tubular mesh could conform to any one of the probes that has been chosen for the patient. The anterior and/or posterior surface of the solid probe may be flat or convex, which may permit easier access while suturing. The probe may also be made in other shapes, such as rectangular, to define the anterior and posterior surfaces with greater prominence. The probe may be single, or there may be several different sizes to accommodate different patients, since the depth and width of the vagina may vary to some extent. Each probe may have a handle attached so that it may be manipulated during surgery (e.g. tilted up or down, or side to side) to facilitate suturing. It may also be attached to a fixed stand, which may be affixed to the surgical table. The probes may be reusable or disposable and may be constructed of plastic, metal or other hard material.

For sacrocervicopexy, the probe may have a different configuration: one that would accommodate the cervix. The probe may include an inner channel that would either act as an access port for the cervical trocar, or would act as the actual access port for the cervix. If this latter embodiment is utilized, the access port would need to have a valve system that would maintain intraabdominal pressure (pneumoperitoneum) whether or not an instrument was placed inside the port, as is the case with laparoscopic trocars. Alternatively, the probe may have an anterior and posterior surface, and have a hollow portion in the middle that could accommodate the cervical trocar (access port).

FIG. 1 demonstrates the basic configuration of the tubular mesh for sacrocolpopexy. The design has a conical structure (1) to surround the entire circumference of the vaginal vault (2). This design may be altered by the surgeon by cutting some mesh out, depending on the individual patient's anatomy. There is also an extension (10) that extends to the sacrum for apical suspension.

Figure 2:
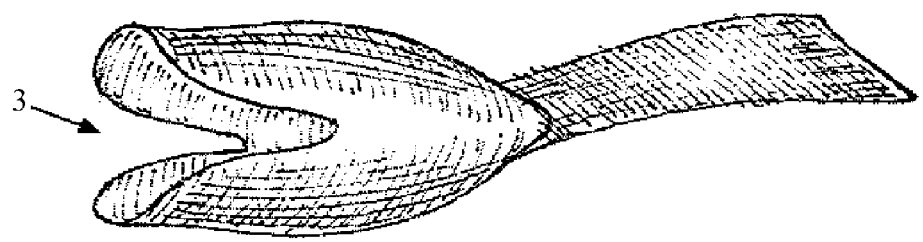
FIG. 2 demonstrates an alternative configuration of the tubular mesh with cut outs for lateral tissue that cannot be dissected.

FIG. 2 demonstrates an alternative configuration (or a customized configuration created by the surgeon) of the tubular mesh with the lateral portions cut out (3) to allow for tissue that cannot be dissected by the surgeon.

Figure 3:
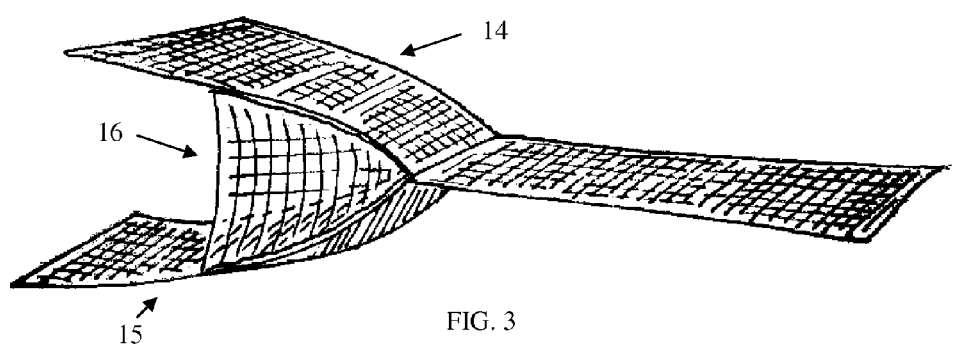
FIG. 3 demonstrates an example of a Y-shaped mesh with mesh material on the lateral sides attaching the anterior and posterior mesh extensions.

FIG. 3 demonstrates a Y-shaped configuration of the mesh, with anterior (14) and posterior (15) extensions, and a separate piece of material (16) that acts as a bridge between the anterior and posterior extensions, maintaining a tubular shape to the mesh. This separate element may be present on both lateral aspects of the mesh and may be incised or excised after fixation sutures are placed in the mesh.

Figure 4:
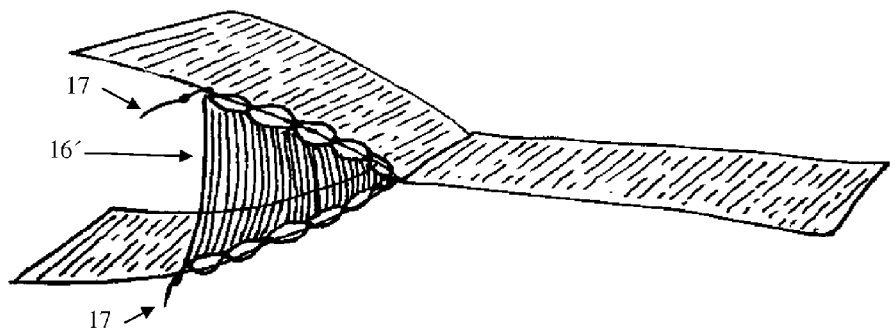
FIG. 4 demonstrates an alternative configuration of the lateral mesh segments that are held in place by a single suture on each side, so they can be removed, if desired, by cutting the one suture on each side, which slides out of the mesh and can be removed from the patient.

FIG. 4 demonstrates a Y-shaped configuration of the mesh, with anterior and posterior extensions, and a separate piece of material (16') that acts as a bridge between the anterior and posterior extensions, maintaining a tubular shape to the mesh. This separate element may be present on both lateral aspects of the mesh and may be removed by cutting one or more sutures (17) which releases the lateral elements.

Figure 5:
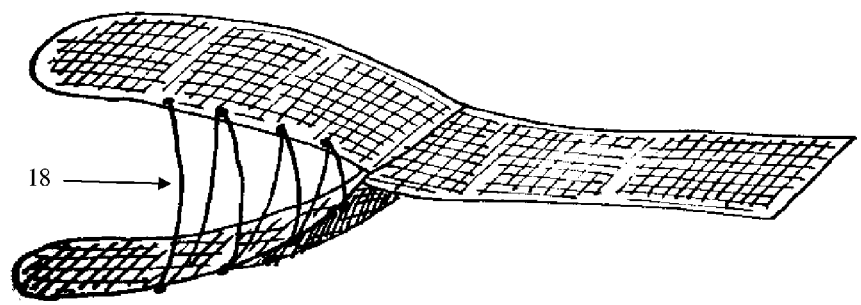
FIG. 5 demonstrates a Y-shaped mesh with a suture woven into the anterior and posterior mesh segments in a "zig-zag" or "shoelace" configuration so that it can be cut and removed after placement of fixation sutures.

FIG. 5 demonstrates a Y-shaped configuration of the mesh, with anterior and posterior extensions, and a separate suture (18) that acts as a bridge between the anterior and posterior extensions, maintaining a tubular shape to the mesh. This separate suture may be present on both lateral aspects of the mesh and is woven into the lateral aspects of the gap between the anterior and posterior mesh extensions in a "zig-zag" or "shoelace" manner, such that it may be removed by cutting the suture, which then unravels it from the mesh.

Figure 6:
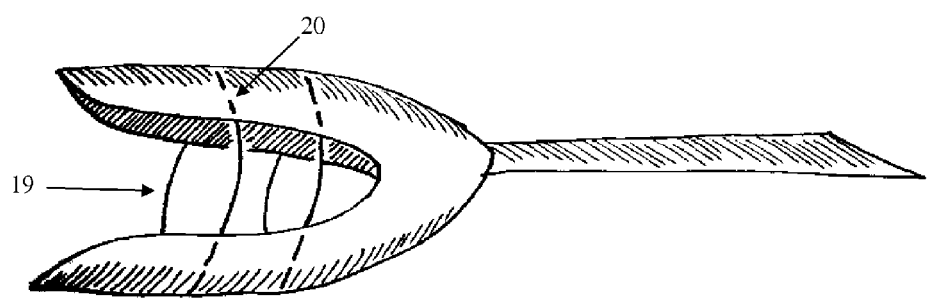
FIG. 6. Demonstrates a Y-shaped mesh with sutures or elastic bands that encircle the two sides (anterior and posterior) and can later be cut and removed.

FIG. 6 demonstrates a tubular shaped mesh similar to that shown in FIG. 2, but that further includes one or more sutures or elastic bands (19) that encircle the anterior and posterior mesh extensions. These encircling elements may be woven (20) into the mesh or may otherwise be attached to the anterior and posterior extensions. These elements may be cut after fixation sutures have been placed. Cutting an element allows the element to be removed in one piece. Of note, this embodiment may use a traditional Y-shaped mesh rather than a tubular shaped mesh.

Figure 7:
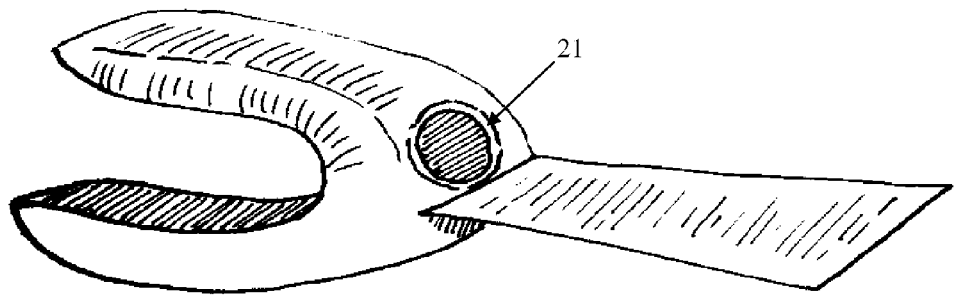
FIG. 7 demonstrates a tubular mesh configuration with a reinforced hole at the proximal end of the vaginal coverage area to allow instruments placed through the cervix to come through the hole.

FIG. 7 demonstrates a tubular shaped mesh that has a cut out (21) at the proximal portion of the vaginal mesh (the area where the cervix or vaginal apex would be located), through which surgical devices such as trocars, mesh, needles or sutures, may be placed into the abdominal/pelvic cavity from the vagina.

Figure 8:
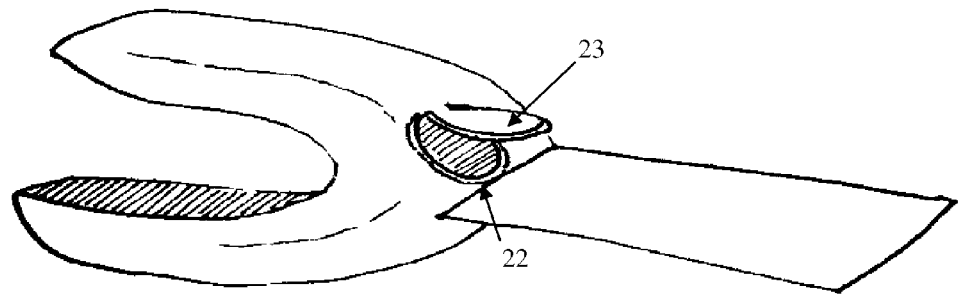
FIG. 8 demonstrates a tubular mesh configuration with a reinforced hole with a mesh flap at the proximal end of the vaginal coverage area to allow instruments placed through the cervix to come through the hole.

FIG. 8 demonstrates an alternative configuration of the tubular shaped mesh that has a cut out (22) with a flap (23) at the proximal portion of the vaginal mesh (the area where the cervix or vaginal apex would be located), through which surgical devices such as trocars, mesh, needles or sutures, may be placed into the abdominal/pelvic cavity from the vagina.

Figure 9:
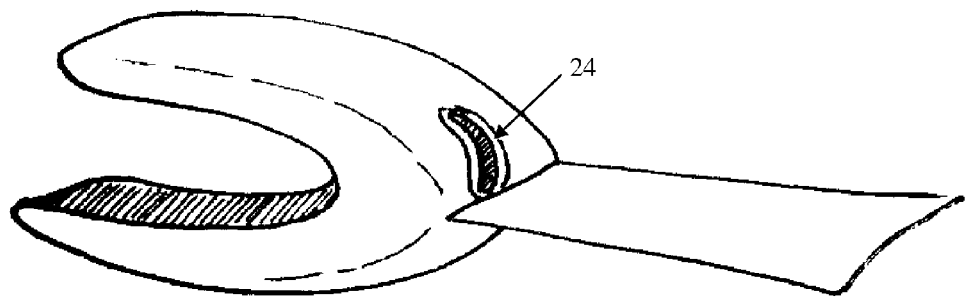
FIG. 9 demonstrates a tubular mesh configuration with a reinforced slit at the proximal end of the vaginal coverage area to allow instruments placed through the cervix to come through the hole.

FIG. 9 demonstrates another embodiment of the configuration of the tubular shaped mesh that has a vertical, horizontal or oblique slit (24) at the proximal portion of the vaginal mesh (the area where the cervix or vaginal apex would be located), through which surgical devices such as trocars, mesh, needles or sutures, may be placed into the abdominal/pelvic cavity from the vagina.

Figure 10:
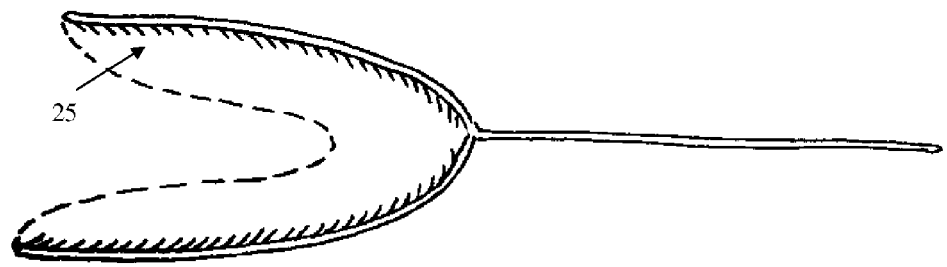
FIG. 10 demonstrates a cross section of a tubular shaped mesh with unidirectional barbs extending out from the inner surface of the mesh. These barbs or projections may be made of the same permanent monofilament material as the mesh itself, or may be made of absorbable monofilament material, such as polydioxinone.

FIG. 10 illustrates a cross-section of the tubular shaped mesh with unidirectional barbs (25) or projections on the inner surface of the tubular or "Y-shaped" mesh that adhere or grab on to the vaginal wall, which may be assisted by a probe placed in the vagina. The barbs or projections may be permanent or absorbable and may be reinforced with fixation sutures.

Figure 11:
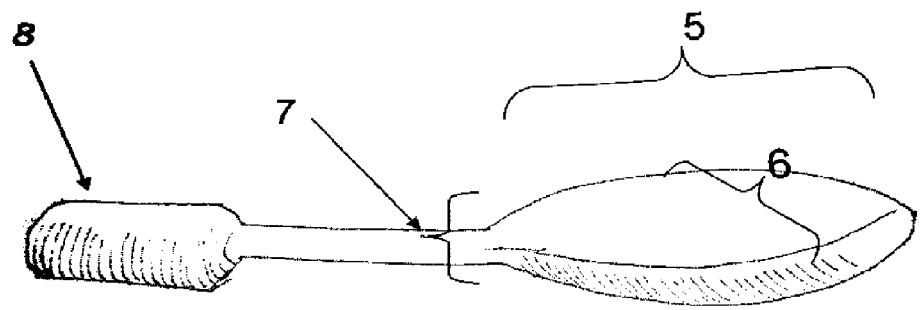
FIG. 11 demonstrates an example of the solid probe.

FIG. 11 shows the basic configuration of the vaginal probe, which is oblong in depth (5), flatter on the anterior (6) and posterior surface, and narrower from the anterior to posterior direction (7). The probe has a handle (8) that can be manipulated by the surgeon to move the probe in any direction to assist with dissection and suturing.

Figure 12:
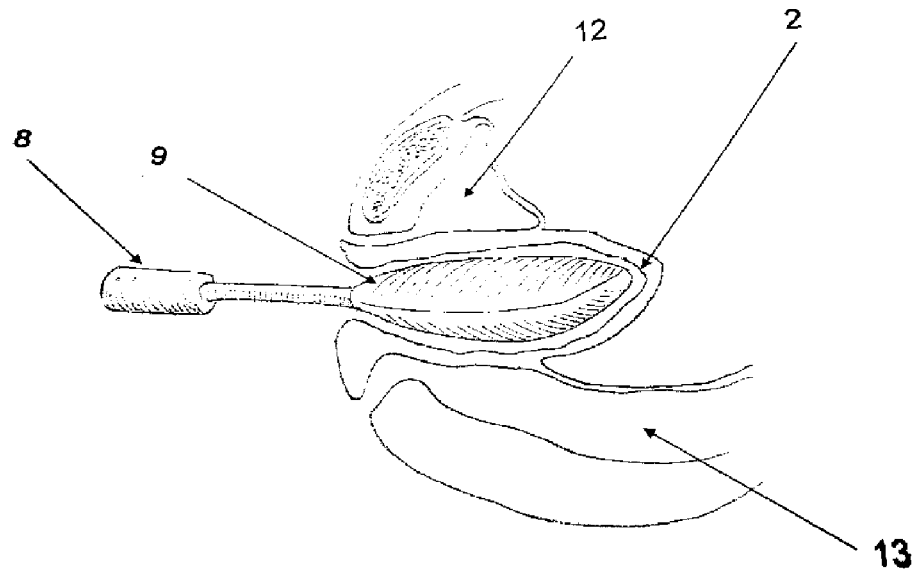
FIG. 12 is a schematic showing a solid probe in the vagina, which delineates the anterior and posterior vagina

FIG. 12 demonstrates the solid probe (9) with its handle (8) in the vagina (2). The bladder (12) is located anteriorly and the rectum (13) is posterior.

Figure 13:
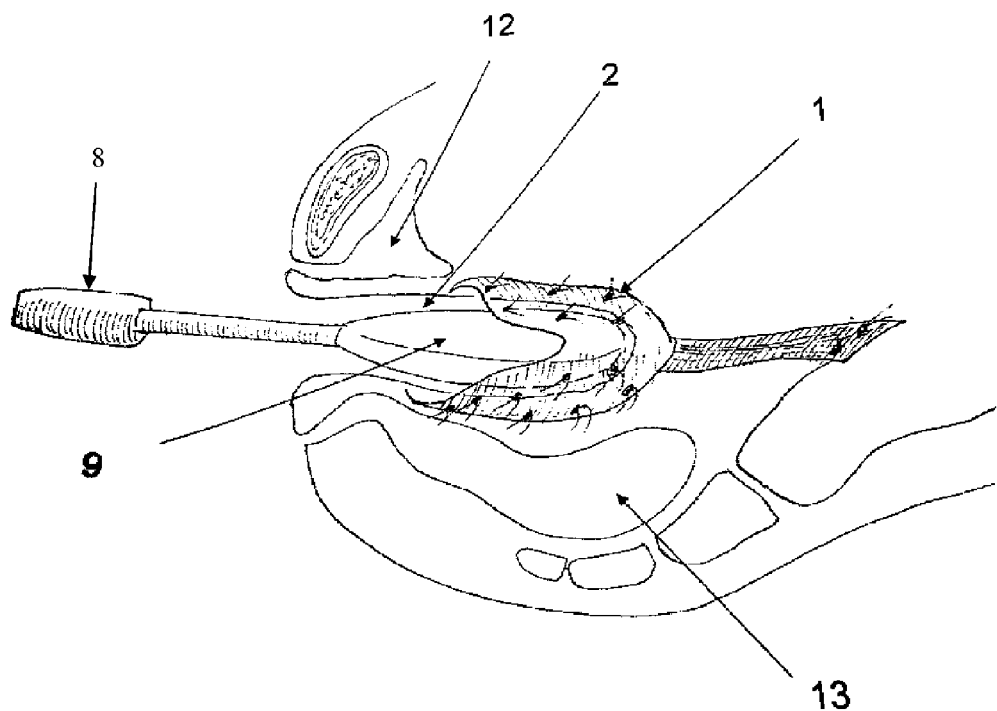
FIG. 13 shows the solid probe in the vagina with the tubular mesh lying over the vagina.

FIG. 13 demonstrates the solid probe (9) in the vagina (2) and the conical-shaped mesh (1) over the vaginal vault, which assists with suturing. The bladder (12) and rectum (13) have been dissected away from the endopelvic fascia.

Figure 14:
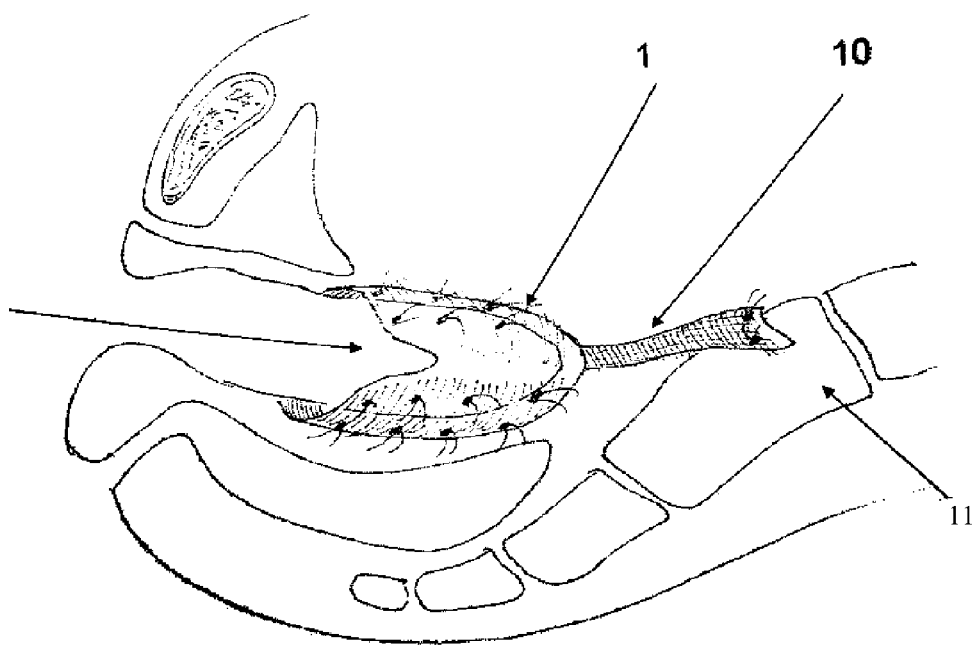
FIG. 14 demonstrates the final position of the mesh on the vaginal vault and attached to the sacrum.

FIG. 14 demonstrates the final position of the tubular mesh configuration with the tubular mesh (1) attached to the vaginal vault (2) and the extension (10) attached to the sacrum (11). The tubular mesh extends along approximately half the length of the vaginal fascia.

Figure 15:
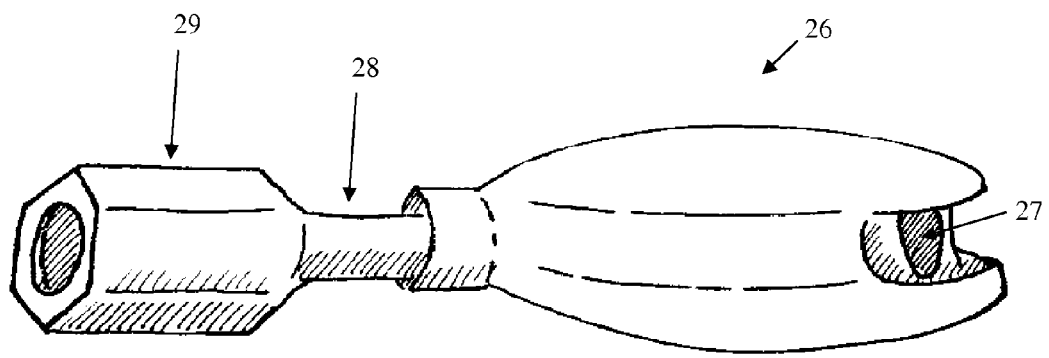
FIG. 15 demonstrates a vaginal delineation probe with an access port for the cervix, in order to introduce and remove surgical devices, such as mesh, sutures, or needles into and from the pelvic/abdominal cavity. The probe would have an indentation to accommodate the cervix and the hollow tube may either allow insertion of a separate access port, or may be the access port, with a valve in the tube to prevent loss of pneumoperitoneum with or without instruments placed through the tube.

FIG. 15 demonstrates one embodiment of a vaginal probe (26) that may be used after laparoscopic or robotic supracervical hysterectomy. There is a channel (27) that runs through the center of the probe through which surgical devices may be inserted and removed from the abdominal/pelvic cavity. The probe has a shaft (28) and a handle (29) and may have a valve that prevents loss of pneumoperitoneum. This configuration may also be used for sacrocolpopexy if the surgeons wishes to make a small incision at the apex of the vagina to introduce surgical devices through the vagina and into the abdominal/pelvic cavity.

I claim:

1. A mesh for sacrocolpopexy or sacrocervicopexy, comprising:
    a sacral portion comprising a flap of mesh; and
    a vaginal portion attached to the sacral portion and comprising:
        an anterior portion comprising a flap of mesh;
        a posterior portion comprising a flap of mesh attached to and extending away from the anterior portion, so that it is spaced apart from the anterior portion; and
        support material attaching each lateral edge of the anterior portion to a corresponding lateral edge of the spaced-apart posterior portion;
        such that the anterior portion, the posterior portion, and the support material define a tubular sleeve sized and shaped for surrounding, lying flat against, and conforming to a vaginal fascia, extending along approximately half the length of the vaginal fascia, and maintaining contact with the vagina during sacrocolpopexy or sacrocervicopexy without slipping.

2. The mesh of claim 1, wherein mesh is not present in lateral cutouts extending along part of the vaginal portion from a distal free end of the vaginal portion.

3. The mesh of claim 1, wherein the sacral portion, the anterior portion, and the posterior portion form a Y shape, and the support material comprises mesh spanning the anterior and posterior portions on each side.

4. The mesh of claim 3, wherein the support material is secured to at least one of the anterior portion and the posterior portion by one or more sutures.

5. The mesh of claim 1, wherein the support material comprises sutures or elastic bands woven through the anterior and posterior portions.

6. The mesh of claim 1, wherein the support material comprises one or more sutures bridging the anterior and posterior portions on each side.

7. The mesh of claim 1, wherein the mesh defines a hole in the vaginal portion.

8. The mesh of claim 7, further comprising a flap covering the hole.

9. The mesh of claim 7, wherein the hole is reinforced.

10. The mesh of claim 1, wherein the mesh defines a reinforced slit.

11. The mesh of claim 1, wherein an inner mesh surface of the vaginal portion comprises unidirectional way barbs oriented to grip a vagina when held in tension.

12. The mesh of claim 1, wherein an inner mesh surface is textured to increase its ability to grip a vagina.

13. A kit comprising the mesh of claim 1 and a vaginal probe, the probe sized and shaped to conform to the vaginal portion of the mesh.

* * * * *